United States Patent

[19]

Jakubowski

[11] Patent Number: 5,980,641

[45] Date of Patent: Nov. 9, 1999

[54] METHODS AND SOLUTIONS FOR CLEANING DENTURES

[76] Inventor: Henryk P. Jakubowski, 66-25 103rd St., Forest Hills, N.Y. 11375

[21] Appl. No.: 08/876,149

[22] Filed: Jun. 13, 1997

[51] Int. Cl.$^6$ ................ A61K 9/46; B08B 3/12
[52] U.S. Cl. .................. 134/1; 134/2; 433/216; 424/434; 424/466
[58] Field of Search ............. 134/1, 2; 433/216; 424/434, 466

[56] References Cited

U.S. PATENT DOCUMENTS

| | | | |
|---|---|---|---|
| Re. 32,771 | 10/1988 | Eoga | 252/99 |
| 4,129,456 | 12/1978 | Longo | 134/1 |
| 4,162,172 | 7/1979 | Longo | 134/1 |
| 4,217,234 | 8/1980 | Krisp et al. | 252/99 |
| 4,409,999 | 10/1983 | Pedziwiatr | 134/95 |
| 4,540,504 | 9/1985 | Eoga | 252/99 |
| 4,701,223 | 10/1987 | Eoga | 134/2 |
| 4,710,233 | 12/1987 | Hohmann et al. | 134/1 |
| 4,806,173 | 2/1989 | Toukan | 134/42 |
| 5,380,530 | 1/1995 | Hill | 424/440 |
| 5,421,353 | 6/1995 | Jakubowski | 134/58 R |
| 5,476,607 | 12/1995 | Eoga et al. | 252/99 |
| 5,529,788 | 6/1996 | De Senna | 424/466 |
| 5,639,795 | 6/1997 | Friedman et al. | 514/772.6 |

*Primary Examiner*—Jill Warden
*Assistant Examiner*—Yolanda E. Wilkins
*Attorney, Agent, or Firm*—Steinberg & Raskin, P.C.

[57] ABSTRACT

A method for cleaning dentures in which a solution of about 5% carboxylic acid, an artificial sweetener and a flavoring is prepared, the dentures are placed therein and agitated. After agitation, the dentures are removed from the solution and are insertable into a wearer's mouth immediately without being rinsed, brushed or soaked. The solution is prepared by placing an amount of 25% a carboxylic acid solution in an amount of water equivalent to five times the amount of the 25% carboxylic acid solution or filling a receptacle with a known amount of water and placing a tablet having the sweetener, flavoring and an amount of carboxylic acid sufficient to provide the amount of water with a 5% carboxylic acid concentration into the receptacle. If used in combination with an ultrasonic cleaning apparatus, the solution is placed in a tank of the ultrasonic cleaning apparatus, and an ultrasonic transducer in the ultrasonic cleaning apparatus directs ultrasonic vibrations into the tank to agitate the dentures.

26 Claims, No Drawings

METHODS AND SOLUTIONS FOR CLEANING DENTURES

FIELD OF THE INVENTION

The present invention relates to methods and solutions for treating dentures and other removable dental appliances in order to clean oral deposits from them in an easy manner and so that the dentures or other dental appliance can be inserted into the wearer's mouth and worn immediately after cleaning without additional rinsing, brushing or soaking thereof

BACKGROUND OF THE INVENTION

In the prior art, there are several methods and solutions for treating dentures and other dental appliances in order to clean and remove oral deposits therefrom, and numerous cleaning solutions to be used in the methods.

For example, U.S. Pat. No. 4,806,173 (Toukan), entitled "Method of Cleaning Dental Appliances, Artificial Dentures", describes a purported method for cleaning artificial dentures by immersing the dentures in a dilute aqueous solution of carboxylic acid such as acetic, succinic, maleic, citric, mandelic or lactic acids. The concentration of the carboxylic acid in the water is in the range of 3% to 10%. The dentures are soaked overnight in the solution and then rinsed and optionally brushed before being reinserted into the wearer's mouth. The carboxylic acid thus acts on the dentures for an extended period of time (overnight) in order to effectuate the removal of oral deposits from the dentures.

U.S. Pat. No. 4,217,234 (Krisp) entitled "Denture Cleansing Tablet and Method of Manufacturing the Same" describes a purportedly fast-acting denture-cleansing tablet including certain materials, specifically aminosulfonic acid, ethylene diamine tetraacetic acid, dialkyl thiourea and a non-ionogenic fluorochemical material in an amount sufficient to achieve a pH in a 1% solution of such formulation in water of 6.3 to 6.5.

U.S. Pat. No. 4,540,505 (Eoga) and Reissue Pat. No. 32,771 issued therefrom entitled "Denture Cleaner Having Improved Dissolution Time and Clarity and Method of Preparation" describe a purported cleansing composition which is compacted into tablet form and is fact-acting. The composition comprises a phosphate salt, a perborate salt mixture including anhydrous perborate and monohydrate perborate, a polymeric fluorocarbon, and a chelating or sequestering agent in specific proportions. The composition is capable of cleansing stained surfaces of dentures in a soaking time of about 5 minutes when the tablet is dissolved in aqueous solution.

U.S. Pat. No. 4,701,233 (Eoga) entitled "Liquid Denture Cleanser Composition and Method of Application" describes a purported sprayable liquid denture cleanser composition comprising an aqueous solution of a detergent, such as a sulfonated, sulfated and sulfoacetate fatty alcohol, and a chelating agent of the amino carboxylate or organo phosphate type. The cleanser is stated to have particular application for the removal of tartar and calculus as well as stains and plaque adhering thereto.

U.S. Pat. No. 5,476,607 (Eoga et al.) entitled "Perborate: Persulfate: Protease Denture Cleanser Powder Composition" describes a purported anhydrous denture cleansing effervescent powder including anhydrous perborate, a perborate monohydrate, a lubricant and compression aid, a monopersulfate, one or more proteolytic enzymes, a sequestering agent, and optionally, excipients, builders, colors, flavors and surfactants.

With respect to patents which relate to the removal of cement from dental appliances and dental instruments, reference is made to U.S. Pat. No. 4,129,456 (Longo) entitled "Method of Removal of Dental Cement", which describes a purported method for treating dental appliances, e.g., temporary bridges and crowns, in order to remove cement from the dental appliances in which the dental appliance is placed in a glass beaker containing a full strength solvent. The full strength solvent is a solution of citric acid in a preferred concentration of 40% (corresponding to the ratio 1:2.5 of grams of citric acid to ml water), or any concentration in the range of 10% (1:10) to 89% (1:1.125). The dental appliance is left in the beaker overnight to soak in the solvent. Optionally, an ultrasonic cleaning apparatus is used during the soaking step. Thereafter, in view of the relatively high concentration of citric acid, the dental appliance must be rinsed with tap water before use by the wearer.

In general, these prior art methods do not provide a quick and easy way to clean dentures, or other removable dental appliances, in a citric acid solution so that the dentures can be worn immediately after the cleaning stage is completed without additional steps, such as a rinsing step, a brushing step and a soaking step. Rather, the prior art methods mentioned above have the disadvantages of requiring soaking of the dentures in a solution overnight, which is considered a relatively long amount of time, or using a highly concentrated citric acid solution, which is potentially hazardous and requires rinsing and possible brushing of the dentures after the cleaning stage. The use of highly concentrated citric acid solution may also require additional safety procedures such as wearing protective gloves and glasses.

OBJECTS AND SUMMARY OF THE INVENTION

It is an object of this invention to overcome of drawbacks of the prior art methods for treating dentures and other removable dental appliances to clean oral deposits therefrom.

It is another object of the invention to avoid the risks in certain prior art methods for treating dentures and other removable dental appliances to clean and remove oral deposits therefrom, such as those associated with the use of a strong acid.

It is another object of the invention to provide new and improved methods for treating dentures by removing daily deposits and accumulations of plaque and food debris therefrom, preventing the formation and development of stains, tartar and calculus deposits on the dentures and completely removing these deposits from old or neglected dentures. It is common for stains, tartar and calculus deposits to be present on dentures, e.g., in view of the lack of time to properly clean the dentures and non-compliance with proper brushing techniques of the dentures predominantly by younger denture wearers or elderly people or people with physical handicaps.

It is still another object of the invention to provide new and improved methods for cleaning dentures which use a safe tablet or solution for daily use formulated from non-toxic chemicals.

It is yet another object of the invention to provide new and improved methods for cleaning dentures and other removable dental appliances in which the dentures or other dental appliance undergo a final cleaning stage in a solution which is safe to digest in full working strength and thus the dentures or other dental appliance are ready immediately after the final cleaning stage to insert into the wearer's mouth without additional brushing or rinsing.

It is another object of the invention to provide new and improved methods for cleaning dentures and other dental appliances which can be performed in a dental office or at home.

In order to achieve these objects and others, in one embodiment of the method in accordance with the invention for cleaning dentures and other removable dental appliances, a solution of about 5% of a carboxylic acid including a carboxylic group, an artificial sweetener and a flavoring is prepared in a receptacle and the dentures are placed therein. The dentures are then agitated such as by subjecting them to ultrasonic vibrations produced by means of an ultrasonic wave generator. After a short time period during which the dentures are agitated, e.g., about 1 hour, the dentures are removed from the solution whereupon they are in condition for immediate insertion into a wearer's mouth without the need for subsequent rinsing, brushing or soaking. The concentration of the carboxylic acid in the solution is low enough to avoid any adverse consequences associated with residual amounts of the same which might remain on the dentures. In certain embodiments, the preferred carboxylic acid is citric acid and one preferred manner to prepare a 5% citric acid solution is to place an amount of 25% citric acid solution in an amount of water equivalent to five times the amount of the 25% citric acid solution to thereby dilute the citric acid to a 5% solution. Alternatively, the receptacle is filled with a known amount of water and a tablet is inserted therein, the tablet having the sweetener, flavoring and an amount of citric acid sufficient to provide the amount of water with a 5% citric acid concentration. In the event that the dentures in the solution are agitated by an ultrasonic wave generator of a conventional ultrasonic cleaning apparatus, the solution and dentures would be placed in the tank of the ultrasonic cleaning apparatus to thereby enable the method in accordance with the invention to be used in conjunction with an existing apparatus.

In another embodiment, the concentration of the carboxylic acid including the carboxylic group in the solution is within a range from about 1% to about 5% carboxylic acid, which solution also includes an artificial sweetener and flavoring. The dentures are placed in this solution in an apparatus which provides agitation, such as that disclosed in U.S. Pat. No. 5,421,353, agitated in the solution to thereby effect the removal of oral deposits, and finally the content of the solution is adjusted to provide a diluted solution of from about 0.375% to about 1.25% carboxylic acid. The dentures may be inserted directly into the wearer's mouth upon removal from the final diluted solution without any further rinsing or cleaning step since at the end of the cleaning cycle (the agitation stage), the working solution is transformed automatically into a pleasant tasting solution.

The artificial sweeteners in the tablets, liquid concentrate or ready-to-use solution may be a common sweetener such as aspartame, although other comparable artificial sweeteners may also be used in the invention.

In accordance with certain embodiments of the invention, the solution of from about 1% to about 5% carboxylic acid, artificial sweetener and flavoring may be preformulated and sold as a ready-to-use solution or obtained by the dissolution of a tablet having these ingredients in a set amount of water. The preferred method, based on ease of use, is to obtain the solution from the dilution of a liquid concentrate.

In an alternative embodiment for cleaning dentures in combination with an existing ultrasonic cleaning apparatus, an initial solution of from about 1% to about 5% of a carboxylic acid, artificial sweetener and flavoring is prepared in a tank of the ultrasonic cleaning apparatus, the dentures are placed in the solution in the tank, ultrasonic vibrations or waves are directed into the solution to agitate the dentures by appropriate control of an ultrasonic wave generator associated with the ultrasonic cleaning apparatus, a portion of the solution is drained from the tank after a first time period during which the dentures are subjected to the ultrasonic vibrations or waves, an additional amount of water is then added to the remaining solution to form a diluted solution having about 0.375% to about 1.25% carboxylic acid. The diluted solution acts as a separating liquid to facilitate the removal of food particles, plaque and mineral deposits from the solution, together with odor-causing bacteria, by lowering the specific gravity of the solution. As in the embodiments mentioned above, the dentures are ready for wear immediately upon removal from the diluted solution. One particular ultrasonic cleaning apparatus which includes a tank in which the solution may be formed and an ultrasonic wave generator to agitate the solution to remove oral deposits from the dentures is described in U.S. Pat. No. 5,432,787 (Jakubowski), incorporated by reference herein.

Significant drawbacks of the prior art are overcome by practicing the methods in accordance with the invention.

With respect to the ease of operation of practicing the methods in accordance with the invention, the dentures are not disinfected, e.g., by placing the dentures in a fluid bath which is circulated through an electrolytic cell having a voltage applied to the electrodes to create anodic oxidation. Indeed, the dentures are not purposefully disinfected in the method in accordance with the invention since they are destined to be worn by the same individual after each cleaning. As such, there is no fear of the transmitting infectious material.

With respect to the ease of production of the solution and specifically the formation of the solution from the tablet, unlike the Eoga patents, viz., U.S. Pat. Nos. 4,540,504, Re. 32,771, 4,701,233 and 5,476,607, the solution may be formed ready-to-use or by the dissolution of a tablet in an aqueous solution which is assisted in certain embodiments by the propagation of ultrasonic waves in the solution. Also, with respect to the composition of the solution and the tablet used to form the solution, the solution in the invention has only three main chemical ingredients whereas by contrast, some of the solutions for cleaning dentures of the above-mentioned patents include about twenty or even thirty different chemical ingredients, e.g., as described in U.S. Pat. Nos. 4,540,504 and 5,476,607. The use of a minimum amount of chemicals in the invention results in lower production costs and the tablets are more reliable and dependable to perform the desired cleaning action.

The carboxylic acid in the initial solution in which the dentures are placed and which is agitated, e.g., by ultrasonic waves, must be at a concentration with the range of 1% to 5%, preferably 5%, to enable the dentures to be cleaned of oral deposits. The use of carboxylic acid at this specific concentration range has not been used heretofore in any of the denture cleaning methods and solutions discussed above, in conjunction with agitation of the dentures, such as by an ultrasonic wave generator. Carboxylic acid has however been used in prior art denture cleaner compositions mainly as an aid in obtaining a clear solution, and not as a cleaning agent per se. For example, the Eoga patents mentioned above, viz., U.S. Pat. Nos. 4,540,504, Re. 32,771, 5,476,607 and 4,701,223, describe the use of carboxylic acid as an aid to obtain a clear solution, together with other components, but not as a cleaning agent. In the methods in accordance with the invention, the initial solution is placed in a sealed tank and therefore the clarity of the solution is not material, whereas for other methods in which the dentures are placed in solutions in clear containers, clarity is very important.

DESCRIPTION OF THE PREFERRED EMBODIMENTS

In a preferred method for cleaning dentures in accordance with the invention, a solution of about 5% carboxylic acid, an artificial sweetener and a flavoring is prepared, the dentures are placed in this solution and subjected to agitation, such as by ultrasonic vibrations, for a first time period, and then the dentures are removed from the solution after the first time period whereupon they are in condition for insertion into a wearer's mouth without the need for subsequent rinsing, brushing or soaking. Instead of ultrasonic vibrations, the agitation of the dentures in the solution may be provided by other forms of agitation which are effective to cause cleansing of the dentures or recognized equivalents thereof.

The solution may be prepared in several different ways. For example, an amount of 25% carboxylic acid solution, including an amount of artificial sweetener and flavoring, can be placed in an amount of water equivalent to five times the amount of the 25% carboxylic acid solution to thereby dilute the carboxylic acid to a 5% solution (the liquid concentrate option). The concentration of the carboxylic acid in the solution may also within the range of about 25% to about 30%. It should be understood that a 5% concentrate can also be manufactured and used directly without the need for any dilution stage.

Another way to obtain the solution is to fill a receptacle with a known amount of water, and place a specially formulated tablet therein, the tablet having the sweetener, flavoring and an amount of carboxylic acid sufficient to provide the amount of water in the receptacle with a 5% carboxylic acid concentration. The tablet is optionally coated with at least one surfactant to aid in cleaning of the dentures specifically by assisting in the removal of the daily accumulation of food debris and plaque on the dentures. A preferred composition of the tablet will have about 10 grams of a carboxylic acid, about 0.1 grams of aspartame and a few drops of flavoring such as lemon or apple flavor. As such, the tablet in dry form will consist of about 90% carboxylic acid, 1% aspartame and the remaining part of the flavoring and coating. When placed in 200 ml of water, the tablet will dissolve to provide a 5% concentration of carboxylic acid.

In an alternative method for treating dentures, an initial solution of from about 1% to about 5% carboxylic acid, artificial sweetener and flavoring is prepared and placed in a receptacle, such as a tank of an ultrasonic cleaning apparatus. The dentures are placed in the initial solution in the receptacle and subjecting to ultrasonic vibrations for a first time period. In this method, water is added to the initial solution in one or more intermediate diluting steps prior to the removal of the dentures from the tank and the wearer's insertion thereof into his or her mouth. To this end, for each diluting step, a portion of the solution in the receptacle is removed and replaced by a fresh amount of water or another solution. The water may be flavored or the solution may be flavored. If water is used, then the resultant solution automatically turns into a pleasant-tasting solution (comparable in certain respects to mouthwash) without any additional ingredients. During the intermediate diluting steps, the denture-containing solution may optionally be subjected to ultrasonic vibrations for a relatively short time period to mix the solution. The amount of initial solution removed and water added to the remaining portion may be regulated such that the final solution has a 0.375% to 1.25% carboxylic acid concentration.

Another method for treating dentures is achieved in conjunction with a conventional ultrasonic cleaning apparatus having a tank and an ultrasonic wave generator for directing ultrasonic waves into the tank. In this embodiment, the initial solution of from about 1% to about 5% carboxylic acid, artificial sweetener and flavoring is prepared, e.g., by means of the liquid concentrate or tablet formulation discussed above, and placed in the tank and the dentures are then inserted into the solution. The tank is closed in its conventional manner and the ultrasonic wave generator is activated to subject the dentures in the initial solution to ultrasonic vibrations for a time period set by a controller of the ultrasonic wave generator. The tank is opened after the first time period, and the dentures are removed from the tank. In view of the specific formulation of the solution, the dentures are cleaned and in condition for insertion into a wearer's mouth immediately upon removal from the tank without the need for additional rinsing, brushing or soaking. The initial solution is optionally diluted in one or more intermediate diluting steps prior to removal of the dentures from the tank and insertion thereof by the wearer into his or her mouth. For each diluting step, a portion of the solution in the tank is removed, preferably after the solution settles so that sediment falls to the bottom of the tank and whereby the sediment of the remaining solution is then removed from a bottom of the tank through an outlet valve arranged thereat (e.g., the tank is constructed in accordance with the teachings of U.S. Pat. No. 5,421,353). An equal amount of fresh water or another solution is then passed into the tank to mix with the remaining solution therein.

Some carboxylic acids which may be included in the tablets or solution discussed above are citric acid (which is the preferred carboxylic acid), acetic acid, lactic acid, gluconic acid, sodium chloride, ethylene-diamine-tetraacetic acid (EDTA), and laevulinic acid. As an alternative to a carboxylic acid, it is possible to use other organic acids and associated compounds such as those formed from calcium or magnesium and acetic acid, citric acid, lactic acid, gluconic acid, sodium chloride, (EDTA), and laevulinic acid, e.g., $Ca(CH_3COO)_2$, $Ca(HOOCCH_2 C(OH)CH_2COOH)$, $CA(CH_3CH(OH)COO)_2$, $CaCl_2$, $Ca(HOCH_2(CHOH)_4COO)_2$ and $Ca((HOOCCH_2)_2NCH_2CH_2(CH_2COOH)_2)$. EDTA may be in the form of sodium or ammonium salts at pH above 7. Although these organic acids may be used in accordance with the invention, citric acid is the most useful in view of its neutral flavor and lack of a strong smell in the concentrations used in accordance with the invention (the other acids often having a somewhat strong smell as well as distinct aroma). However, when using color versions of the solution, e.g., in or as a substitute for mouthwash, it might be optimum to use gluconic acid as the carboxylic acid because it has a weak kind of orange color. Also, it might be possible to use different combinations of two or more of the carboxylic acids mentioned above to attain the desired percentage concentration of carboxylic acid. Optionally, alcohol could be used as an aid in improving the flavor. However, no significant improvement in the cleaning cycles of the dentures has been observed using alcohol.

The following examples describe different preparations of tablets used to form the initial solution of citric acid, sweetener and flavoring, each being designed for a particular use.

EXAMPLE 1

Heavy Duty Tablet (to provide an initial 5% citric acid concentration)

This type of tablet is preferred for introductory use with old and neglected dentures having stains, a build-up of tartar and calculus, but may of course be used regularly for cleaning dentures. The working concentration of the citric acid is going to be achieved based on the size of cleaning tank and the amount of water poured therein, for this example, a 200 ml. tank completely filled with water. The tablet will comprise about 10 grams of citric acid, a certain amount of sweetener, such as the amount of aspartame in eight standard tablets of EQUALS™, or an equivalent amount of another sweetener, a few drops of flavoring agent in order to obtain a desired flavor or taste such as apple, lemon or any other desirable flavor. The tablet may optionally be provided with a protective coating with optional surfactant to help clean daily accumulation of food debris and plaque. One minor irritation with this heavy duty tablet is that it will cause a slight burning when wet or itching sensation when touched if not coated adequately in view of the high concentration of citric acid.

In the method using this tablet, the tank of the ultrasonic cleaning apparatus is filled with about 200 ml water and the dentures and tablet are placed in the tank which is subjected to an ultrasonic cleaning cycle which runs for approximately one hour. After one hour, the apparatus is programmed to cease generating ultrasonic waves for about 15 minutes so that during this calm period, sediments collect on the bottom of the tank. Thereafter, the solution is optionally diluted one or more times by opening a valve associated with the tank of the ultrasonic cleaning apparatus to allow about 50% of the solution in the tank to flow therefrom. For each diluting step, the tank is then filled with an amount of water equal to the amount of solution removed from the tank. The apparatus is turned on in an ultrasonic cleaning cycle, i.e., during which ultrasonic waves are produced to again agitate the diluted solution, for about 5 minutes to mix the solution which comprises 50% of the previously agitated solution and 50% new water. The apparatus is then turned off and the dentures remain in the tank for about 15 minutes. After this time, the valve is opened again and about 50% of the existing solution in the tank is removed. The tank is then filled with an amount of fresh water or a solution such as mouthwash from a reservoir equal to the amount of solution removed from the tank. At this stage, the dentures have been cleaned and are ready for use by the wearer upon opening the ultrasonic apparatus.

The amount of water being removed from the tank, and thus the amount of fresh water being inserted into the tank, may be regulated to vary the final concentration of citric acid in the solution. In this manner, it is possible to attain a final solution having a 1.25% citric acid concentration in view of the two diluting stages. It should also be pointed out that the diluting stages are not absolutely required and that the dentures may be worn after the initial ultrasonic cleaning stage, possibly after the sediment settling stage, even when the solution has a 5% citric acid concentration since this relatively low concentration does not cause harm to the wearer.

EXAMPLE 2

Regular Usage Tablet (to provide an initial 1.25% citric acid concentration)

This type of tablet is preferred for use with new or previously cleaned dentures since in these cases, it provides the most effective cleaning. The tablet will comprise about 2.5 grams of citric acid, a certain amount of sweetener such as the amount of aspartame in six to eight standard tablets of EQUAL™, or an equivalent amount of another sweetener, a few drops of flavoring agent in order to obtain a desired flavor or taste such as apple, lemon, mint or any other desirable flavor. The tablet may optionally be provided with a protective coating with optional surfactant to help clean daily accumulation of food debris and plaque.

In one cleaning method using this tablet, the tank of the ultrasonic cleaning apparatus is filled with about 200 ml water and the dentures and the tablet are placed in the tank, the tank is closed and an ultrasonic cleaning cycle is initiated and runs for approximately one hour. After one hour, the apparatus is programmed to cease generating ultrasonic waves for about 15 minutes so that during this calm period, sediments collect on the bottom of the tank. Thereafter, if the solution in the tank is to be subjected to optional diluting stages, a valve associated with the tank of the ultrasonic cleaning apparatus is opened to allow about 50% of the solution in the tank to be drained therefrom. The tank is then filled with an amount of fresh water equal to the amount of solution removed from the tank. The apparatus may optionally be turned on in an ultrasonic cleaning cycle, i.e., during which ultrasonic waves are produced to again agitate the diluted solution, for about 5 minutes to mix the solution which comprises 50% of the previously agitated solution and 50% fresh water. The apparatus is then turned off. Whether the short ultrasonic cleaning cycle is run or not, the dentures are allowed to remain undisturbed in the tank for about 15 minutes after the fresh water is added, during which sediments collect at the bottom of the tank. After this time, the valve is opened again and about 50% of the existing solution in the tank is drained from the tank. The tank is then filled with an amount of fresh water or a solution such as mouthwash from a reservoir equal to the amount of solution removed from the tank. If water is used, then the resultant solution automatically turns into solution comparable in certain respects to mouthwash without any additional ingredients. At this stage, the dentures have been cleaned and are ready for use by the wearer upon opening the ultrasonic apparatus without requiring any rinsing.

It is possible to regulate the amount of water being removed from the tank, and thus the amount of fresh water being inserted into the tank to vary the final concentration of citric acid in the solution. In this manner, it is possible to attain a final solution having a 0.375% citric acid concentration in view of the two diluting stages.

EXAMPLE 3

Medium Duty Tablet (to provide an initial 2.5% citric acid concentration)

This type of tablet is preferred for use with moderately stained dentures and moderate deposits of calcium. The tablet will comprise about 5 grams of citric acid, a certain amount of sweetener such as the amount of aspartame in eight standard tablets of EQUAL™, or an equivalent amount of another sweetener, a few drops of flavoring agent in order to obtain a desired flavor or taste such as apple, lemon or any other desirable flavor. The tablet may optionally be provided with a protective coating with optional surfactant to help clean daily accumulation of food debris and plaque.

In the preferred method using this tablet, the tank of the ultrasonic cleaning apparatus is filled with about 200 ml water and the dentures and the tablet are placed in the tank, the tank is closed and an ultrasonic cleaning cycle is initiated and runs for approximately one hour. After one hour, the apparatus is programmed to cease generating ultrasonic waves for about 15 minutes so that during this calm period, sediments collect on the bottom of the tank. Thereafter, a valve associated with the tank of the ultrasonic cleaning apparatus will be opened to allow about 50% of the solution in the tank to be drained therefrom. The tank is then filled with an amount of fresh water equal to the amount of solution removed from the tank. The apparatus may optionally be turned on in an ultrasonic cleaning cycle, i.e., during which ultrasonic waves are produced to again agitate the diluted solution, for about 5 minutes to mix the solution which comprises 50% of the previously agitated solution and 50% fresh water. The apparatus is then turned off. Whether the short ultrasonic cleaning cycle is run or not, the dentures are allowed to remain undisturbed in the tank for about 15 minutes after the fresh water is added. After this time, the valve is opened again and about 50% of the existing solution in the tank is drained from the tank. The tank is then filled with an amount of fresh water from a reservoir thereof or a solution such as mouthwash from a reservoir equal to the amount of solution removed from the tank. At this stage, the dentures have been cleaned and are ready for use by the wearer upon opening the ultrasonic apparatus without requiring any rinsing.

Clinical and Laboratory Tests

The tests for safety of the cleaning materials on the dental alloys, denture acrylics and plastics and dental porcelains accumulated total cleaning time in excess of fifteen years exposure of the dentures in cleaning solution without traces of deterioration, bleaching or staining acrylics, plastics or porcelains. No traces of corrosion or staining were detected on dental alloys. Laboratory tests were performed on standard materials by outside chemical laboratory with the following results:

Stain Removes of Key and Tartar Removers

|  | Iodine Gentian | Violet | Tea | Total Cleaning Time |
| --- | --- | --- | --- | --- |
| Jakubowski 5% | 2.5 | 3 | 1 | 6.5 |
| Bayer T&S | 8.5 | 2 | 0.5 | 11 |
| Sultan T&S | 2.5 | 8.8 | 1 | 12.3 |
| Stain Kleen | 2.25 | 9 | 1.17 | 12.4 |
| Jakubowski 2.5% | 3.17 | 9.25 | 1.17 | 13.6 |
| L&R | 10 | 8 | 0.83 | 18.83 |
| Jakubowski 1.25% | 11 | 11 | 1.17 | 24 |
| Water H2O | 35 | 11 | 1 | 47 |

From this chart, it is seen that the method for cleaning dentures in accordance with the present invention, using either the heavy duty tablet, the regular use tablet or the medium duty tablet, provides a comparable degree of stain removal as existing denture cleaning agents but provides one particularly advantageous benefit, namely it does not require rinsing of the dentures after the cleaning process. Rather, at the end of the cleaning process in accordance with the invention, the final solution constitutes a pleasant-tasting solution comparable to mouthwash and the dentures are ready for wear and in fact, may even be provide with some flavor in view of the presence of the mouthwash in the final stage of the cleaning process.

When used in particular with the ultrasonic apparatus described in U.S. Pat. No. 5,432,787, a measured amount of water is put into the tank through the inlet valve, and tablet and dentures are then placed into the water in the tank. The cover of the tank is closed and the controller activates the ultrasonic transducer to provide a cleaning cycle for a set time duration, e.g., one hour. The controller, via its timing means, then keep the dentures and the initial solution for a predetermined soak time, e.g., 15 minutes. The controller is then programmed to open the outlet valve of the tank to allow the working solution to drain from the tank. The outlet valve is then closed and water from the reservoir tank is allowed to flow into the tank to fill the tank up again through the appropriate coordination of the reservoir tank valve. The ultrasonic transducer may be programmed to provide a short span of ultrasonic vibrations to this new solution. The new solution is kept for a predetermined time duration to allow for particulate matter to settle on the bottom of the tank, which is facilitated by through the lowering of the specific gravity of the solution. Again, the outlet valve of the tank is opened to allow the solution to be removed and then fresh water is added from the reservoir tank through the operation of the reservoir tank valve. The cover of the tank is then openable to access cleaned dentures ready immediately for wear. It is pointed out that all of the steps concerning the operation of the ultrasonic transducer and valves may be accomplished by programming the desired sequence of steps onto the ROM chip in the controller.

The examples provided above are not meant to be exclusive. Many other variations of the present invention would be obvious to those skilled in the art, and are contemplated to be within the scope of the appended claims. For example, it should be recognized and appreciated that if one or more diluting step are to be performed in a denture cleaning method described above, then the initial solution may be provided with an increased concentration of sweetener and flavorings so that after the diluting step(s), the resultant solution will have a desired flavor and sweetness. Thus, the initial solution may be "over-concentrated" by increasing the amount of sweetener and flavoring in the solution or the amount of the sweetener and flavoring in the tablet.

I claim:

1. A method for cleaning dentures, comprising the steps of:

preparing a solution of about 5% of a carboxylic acid having a carboxylic group, an artificial sweetener and a flavoring said solution being digestible;

placing the dentures in the solution;

agitating the dentures in the solution for a first time period; and removing the dentures from the solution after the first time period whereupon the dentures are in condition for insertion into a wearer's mouth without the need for subsequent rinsing, brushing or soaking.

2. The method of claim 1, wherein the step of preparing the solution comprises the step of:

placing a 25% carboxylic acid solution in an amount of water equivalent to five times the amount of the 25% carboxylic acid solution to thereby dilute the 25% carboxylic acid solution to a 5% carboxylic acid solution.

3. The method of claim 1, wherein the step of preparing the solution comprises the steps of:

filling a receptacle with a known amount of water, and placing a tablet having the sweetener, flavoring and an amount of the carboxylic acid sufficient to provide the amount of water with a 5% carboxylic acid concentration into the receptacle.

4. The method of claim 1, wherein the artificial sweetener is aspartame.

5. The method of claim 1, further comprising the step of:

placing the solution in a tank of an ultrasonic cleaning apparatus having an ultrasonic transducer, and wherein the step of agitating the dentures comprises the step of controlling the ultrasonic transducer to direct ultrasonic vibrations into the tank.

6. The method of claim 1, wherein the carboxylic acid is selected from the group consisting of citric acid, acetic acid, lactic acid, gluconic acid, sodium chloride, ethylenediamine-tetraacetic acid (EDTA), and laevulinic acid.

7. The method of claim 1, wherein the carboxylic acid is citric acid.

8. A method for cleaning dentures, comprising the steps of:
preparing an initial solution of from about 1% to about 5% of a carboxylic acid having a carboxylic group, artificial sweetener and flavoring in a receptacle, said solution being digestible,
placing the dentures in the initial solution in the receptacle,
agitating the dentures in the initial solution for a first time period,
diluting the initial solution after the first time period by removing a portion of the initial solution and adding water to the remaining portion of the initial solution to form a first separating solution, and then
removing the dentures from the first separating solution whereupon the dentures are in condition for insertion into a wearer's mouth without the need for subsequent rinsing, brushing or soaking.

9. The method of claim 8, wherein the step of agitating the dentures comprises the step of subjecting the dentures to ultrasonic vibrations for the first time period, further comprising the step of:
subjecting the dentures in the first separating solution to ultrasonic vibration for a second time period.

10. The method of claim 8, further comprising the steps of:
removing a portion of the first separating solution from the receptacle while the dentures are still in the first separating solution, and
adding a second amount of water to the remaining portion of the first separating solution to form a second separating solution.

11. The method of claim 8, wherein the step of preparing the solution comprises the step of:
placing an amount of a 25% carboxylic acid solution in an amount of water equivalent to five times the amount of the 25% carboxylic acid solution to thereby dilute the carboxylic acid to a 5% solution.

12. The method of claim 8, wherein the step of preparing the solution comprises the steps of:
filling the receptacle with a known amount of water, and
placing a tablet having the sweetener, flavoring and an amount of the carboxylic acid sufficient to provide the amount of water with a 5% carboxylic acid concentration into the receptacle.

13. The method of claim 12, further comprising the step of coating the tablet with at least one surfactant to aid in cleaning of the dentures.

14. The method of claim 8, wherein the carboxylic acid is selected from the group consisting of citric acid, acetic acid, lactic acid, gluconic acid, sodium chloride, ethylenediamine-tetraacetic acid (EDTA), and laevulinic acid.

15. The method of claim 8, wherein the carboxylic acid is citric acid.

16. The method of claim 8, wherein the receptacle is a tank of an ultrasonic cleaning apparatus, further comprising the step of
arranging an ultrasonic transducer in the ultrasonic cleaning apparatus to direct ultrasonic vibrations into the tank.

17. The method of claim 8, further comprising the step of
maintaining the dentures in the initial solution after the first time period for a third time period to let sediments settle on a bottom of the receptacle, the portion of the initial solution being removed from the receptacle at a location proximate the bottom of the tank such that the sediments are removed from the receptacle.

18. The method of claim 8, wherein the initial solution is a 5% carboxylic acid solution.

19. The method of claim 8, wherein the step of diluting the initial solution comprising the step of:
regulating the amount of initial solution removed and water added to the remaining portion such that the first separating solution has a 0.375% to 1.25% carboxylic acid concentration.

20. A method for cleaning dentures in an ultrasonic cleaning apparatus having a tank and an ultrasonic wave generator for directing ultrasonic waves into the tank, comprising the steps of:
placing an initial solution of from about 1% to about 5% of a carboxylic acid, artificial sweetener and flavoring in the tank said solution being digestible,
placing the dentures in the initial solution in the tank,
closing the tank,
activating the ultrasonic wave generator to subject the dentures in the initial solution to ultrasonic vibrations for a first time period,
opening the tank after the first time period, and then
removing the dentures from the tank, the dentures being insertable into a wearer's mouth immediately upon removal from the tank without being rinsed, brushed or soaked.

21. The method of claim 20, wherein the initial solution is a 5% carboxylic acid solution.

22. The method of claim 20, wherein the step of preparing the solution comprises the step of:
placing an amount of a 25% carboxylic acid solution in an amount of water equivalent to five times the amount of the 25% carboxylic acid solution to thereby dilute the carboxylic acid to a 5% solution.

23. The method of claim 20, wherein the step of preparing the solution comprises the step of:
filling the tank with a known amount of water, and
placing a tablet having the sweetener, flavoring and an amount of the carboxylic acid sufficient to provide the amount of water with a 5% carboxylic acid concentration into the receptacle.

24. The method of claim 1, wherein the first time period is at least as short as about one hour.

25. The method of claim 8, wherein the first time period is at least as short as about one hour.

26. The method of claim 20, wherein the first time period is at least as short as about one hour.

* * * * *